United States Patent [19]

Agback et al.

[11] Patent Number: 4,528,367
[45] Date of Patent: Jul. 9, 1985

[54] METHOD AND INTERMEDIATES FOR PREPARING HIGH PURITY 3,3′-AZO-BIS-(6-HYDROXY BENZOIC ACID)

[75] Inventors: Karl H. Agback, Upsala; Alf S. Nygren, Örbyhus, both of Sweden

[73] Assignee: Pharmacia AB, Upsala, Sweden

[21] Appl. No.: 462,356

[22] Filed: Jan. 31, 1983

Related U.S. Application Data

[63] Continuation of Ser. No. 247,402, Mar. 25, 1981, abandoned.

[30] Foreign Application Priority Data

Mar. 26, 1980 [SE] Sweden ................. 8002321

[51] Int. Cl.³ .............. C07C 107/06; C09B 29/01; C09B 29/14; C09B 43/00
[52] U.S. Cl. .................. 534/599; 260/456 A; 260/456 P; 534/583; 534/588; 534/660; 534/730; 534/887
[58] Field of Search .................. 260/207, 208

[56] References Cited

U.S. PATENT DOCUMENTS

| | | | |
|---|---|---|---|
| 1,157,169 | 11/1914 | Mettler | 260/207 |
| 1,848,772 | 3/1932 | Felix | 260/207 |
| 2,690,438 | 9/1954 | Kracker | 260/187 |
| 4,045,429 | 8/1977 | Agback | 260/156 |

*Primary Examiner*—Floyd D. Higel
*Attorney, Agent, or Firm*—Fred Philpitt

[57] ABSTRACT

A method of preparing 3,3′-azo-bis-(6-hydroxy benzoic acid) of formula I

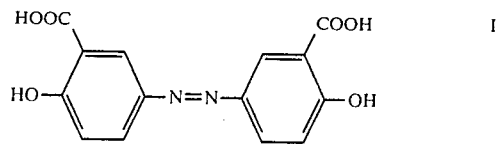

and salts thereof in at least 98% purity for treating inflammatory intestinal diseases. According to the invention a compound II

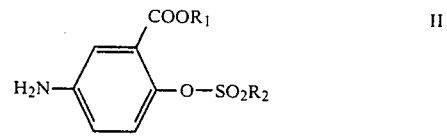

is diazotized, and the diazonium salt obtained is coupled with a compound III

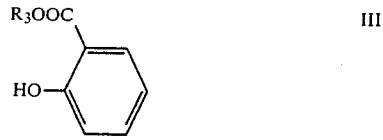

The formed intermediate IV, which is also comprised by the invention,

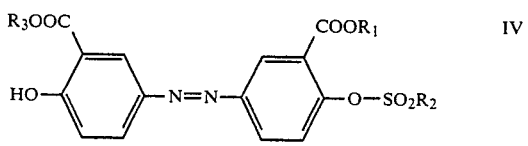

is hydrolized in alkaline medium to form the compound I. $R_1$, $R_2$ and $R_3$ signify lower alkyl, $R_2$ also possibly substituted phenyl.

16 Claims, No Drawings

METHOD AND INTERMEDIATES FOR PREPARING HIGH PURITY 3,3'-AZO-BIS-(6-HYDROXY BENZOIC ACID)

This is a continuation of application Ser. No. 247,402, filed Mar. 25, 1981, now abandoned and the benefits of 35 USC 120 are claimed relative to it.

This present invention relates to a new method and new intermediates for preparing 3,3'-azo-bis-(6-hydroxy benzoic acid) of the formula

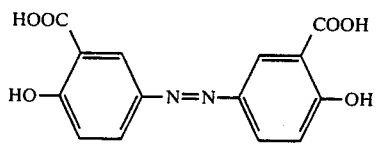

and salts thereof. The new method according to the invention makes it possible to prepare the compound of formula I and its salts, especially pharmaceutically acceptable salts, in very high purity, for example 98% and more, and with good yields.

The compound of formula I is known as such and has found commercial use as a dystuff. A known method for preparing the compound I involves alkaline hydrolysis of 3,3'-azo-6-chloro-6'-hydroxy-dibenzoic acid at high temperature, possibly in the presence of copper: see for example DE Pat. No. 278613. In an alternative known method of preparation the compound in question is prepared by a corresponding alkaline hydrolysis of 3,3'-azo-bis-(6-chlorobenzoic acid): see for example GB Pat. No. 408676. In a third known method of preparation 5-amino salicylic acid is diazotized and coupled with salicylic acid in the presence of trivalent chromium, whereupon the chromium complex formed is decomposed for setting free the compound I: see for example DE Pat. No. 590321.

The first mentioned method of preparation is the one which is used commercially. The product obtained in this hydrolysis of 3,3'-azo-6-chloro-6'-hydroxy-dibenzoic acid is not pure, but contains comparatively great amounts of starting material (e.g. 20 to 30%). Further, the desired end product I is not stable under the severe hydrolysis conditions but is decomposed, i.a. to 5-amino salicylic acid.

It would theoretically be possible to separate the end product I from the starting material, for example by using liquid chromatographic analysis technique. Such separation methods are, however, economically impossible to apply for practical preparative use. Because of the very similar properties of the starting and the end compounds it has not either been possible to separate them by crystallisation.

The alternative synthesis route via the chromium complex of the compound I does not either yield any pure product since impurities of chromium always are present. Because of such impurities the compound I, when prepared in this manner, cannot be used as e.g. a drug.

It is an object of the present invention to provide a technically simple and economically advantageous new method of preparing 3,3'-azo-(bis-6-hydroxy-benzoic acid) of formula I, in which the desired product is obtained in considerably higher purity than in the known methods of preparation. In particular, the invention makes it possible to prepare the compound I in a purity of at least 98%, thereby making it possible to use the compound in question as a drug, for example for treating inflammatory intestinal diseases such as, for example, ulcerous colitis. This use is described in our simultaneously herewith filed patent application Ser. No. 247,252 (corresponding to Swedish Patent Application No. 8002322-9 filed Mar. 26, 1980), herein incorporated by reference.

The method according to the invention is a multi step method for preparing the compound of formula I and salts thereof, starting from compounds of formula II

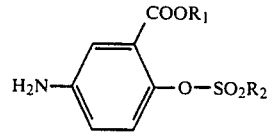

wherein $R_1$ is a lower alkyl group having 1 to 6 carbon atoms, and $R_2$ is a lower alkyl group having 1 to 6 carbom atoms or phenyl or substituted phenyl. Preferred lower alkyl groups are such having 1 to 3 carbon atoms such as methyl. A phenyl group $R_2$ can be mono- or polysubstituted by groups being inert under the reaction conditions, such as alkyl, alkoxy, halogen, etc. Acid addition salts of the compound II can also be used as starting materials, especially salts with a mineral acid or a strong organic acid.

The starting compound of formula II is diazotized in a manner known per se to the corresponding diazonium salt. The diazotation is preferably carried out in conventional manner by treatment with nitrous acid in acid aqueous solution.

The formed diazonium salt of the compound II is then coupled in alkaline solution, preferably in the presence of an alkali metal hydroxide such as a potassium hydroxide, with a compound of the formula III

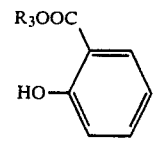

wherein $R_3$ is hydrogen or a lower alkyl group having 1 to 6 carbon atoms, preferably 1 to 3 carbon atoms such as methyl.

The product formed, which corresponds to the formula IV

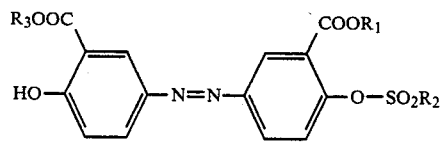

wherein $R_1$, $R_2$ and $R_3$ are as indicated above, is then isolated in a manner known per se, for example by acidifying the reaction mixture to precipitate the product of formula IV. It has been found that the compounds of the formula IV have excellent crystallization properties, thereby making it very simple to purify these compounds to the desired extent by recrystallization. For the recrystallization a great number of inert organic solvents can be used, for example lower aliphatic ketones such as acetone, 2-butanone etc., lower alkanols such as methanol, ethanol etc., aromatic hydrocarbons such as toluene, etc., organic acids and esters such as acetic acid, ethyl acetate, etc., or mixtures thereof.

The compound of formula IV, worked up to the desired purity, is then hydrolized in an aqueous reaction medium to the desired end product of formula I while splitting off the groups —$R_1$, —$R_3$ and —$SO_2R_2$, whereupon the end product of formula I—or salts thereof—are isolated from the reaction mixture. The hydrolysis is preferably carried out in alkaline environment, especially in the presence of an alkali metal hydroxide and possibly an inert, water-miscible solvent, for example alkanones such as acetone, alkanols such as methanol, ethanol, etc. It would be obvious to a person skilled in the art that the hydrolysis conditions can be chosen such that the amounts of partially hydrolized products are minimized while at the same time no significant amounts of secondary by products are formed. It may, as an example, be mentioned that the hydrolysis advantageously can be carried out by boiling in water between 0.5 and 2 h using sodium hydroxide as the base. As mentioned above, and in contrast to the intermediate IV, it is comparatively difficult to purify the end product I, and it is therefore essential that the hydrolysis be carried out in the indicated manner, especially if the end product I is to be used as a drug.

After the hydrolysis has been carried out the end product is isolated from the reaction mixture in a manner known per se, preferably by neutralization or acidification of the reaction mixture, for example by means of a mineral acid such as hydrochloric acid or sulphuric acid, or a strong organic acid such as acetic acid.

The compound of formula I can be isolated as such or in the form of a corresponding salt, preferably a pharmaceutically acceptable salt such as an alkali metal salt. A preferred way of recovering such salts is to partially neutralize the reaction mixture with an acid to a suitable pH for precipitation of the desired salt. For example, the di-sodium and di-potassium salts can be prepared by acidifying the reaction mixture to pH 5–8, preferably 6–7, using a mineral acid or an organic acid such as acetic acid. Alternatively it is, of course, also possible to prepare the desired salts by reacting, in a manner known per se, the isolated acid with any suitable salt forming base.

The starting compounds of formula II used in the method according to the invention can be prepared in accordance with methods known per se or in analogy with methods known per se. For example, the compounds can be prepared by reduction of a corresponding compound of formula V

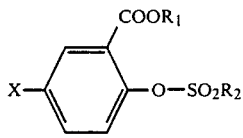

wherein $R_1$ and $R_2$ are as indicated above and X is a group which can be converted into an amino group, for example a nitro or arylazo group.

The invention also comprises compounds of formula IV which—as mentioned above—have proved to posses valuable crystallization properties and because thereof are excellently well suited as intermediates for the preparation of valuable end compounds such as 3,3'-azo-bis(6-hydroxy-benzoic acid) of formula I.

Although the method and the intermediates according to the invention primarily are intended for preparing 3,3'-azo-bis(6-hydroxy-benzoic acid) of pharmaceutically acceptable purity, it would be obvious that they also can be used for preparing this compound for other use, wherein the requirements on purity are not as high.

The invention will now be illustrated in more detail in connection with some special non-limiting examples.

EXAMPLE 1

(Preparation of starting materials)

(a) Methyl-2-methane sulfonyloxy-5-nitro-benzoate.

98.5 g of methyl-2-hydroxy-5-nitro-benzoate were dissolved in 250 ml of pyridine, whereupon 68.5 of methane sulonyl chloride were added. After heating to 50° C. for 10 minutes the solution was poured on 5N ice cooled hydrochloric acid. The oil formed was extracted with chloroform. The chloroform phase was washed with water, dried and evaporated. 50 ml of toluene were added and evaporated. This was repeated once, the oil then crystallizing. Yield: 132 g of the title substance.

(b) Methyl-3-amino-6-methane sulfonyloxy-benzoate.

132 g of the nitro compound from step (a) were hydrogenated in 500 ml of acetic acid and 3 g of 10% palladium-on-carbon at 1–3 at. After the theoretical amount of hydrogen gas had been consumed the mixture was filtered and evaporated. It was dissolved in 1 liter of isopropanol at 65° C., whereupon HCl in ethanol was added. The hydrochloride crystallized upon cooling. After filtering the substance was shaken with sodium carbonate in water and chloroform. The chloroform phase was evaporated. The amine was re-crystalized from methanol/water. Yield: 93 g of the pure title substance.

EXAMPLE 2

(a) Methyl-2-hydroxy-5[(4-methane sulfonyloxy-3-metoxycarbonylphenyl)-azo]-benzoate.

12.2. g of methyl-3-amino-6-methane sulfonyloxy-benzoate (prepared according to Example 1), 75 ml of 2N hydrochloric acid and 200 g of ice were diazotized at 0° C. with 3.5 g of sodium nitrite in 20 ml of water. The diazonium salt solution was rapidly mixed with a freshly prepared solution of 15.2 g of methyl salicylate, 12 g of 85% potassium hydroxide and 1 liter of icewater while stirring vigorously. The coupling solution was acidified with hydrochloric acid after about 15 seconds. The precipitated oily product was extracted with chloroform. After drying, evaporation, and re-crystallization from 2-butanone the title substance was obtained in a yield of 12.8 g (63%). The purity was determined by liquid chromatographic analysis (HPLC) on a "reversed phase"-column ($\mu$-Bondpak $C_{18}$) with methanol/water (75:25) as eluant. The total amount of impurities was only about 0.6 area percent.

(b) 3,3'-azo-bis(6-hydroxy-benzoic acid).

41 g of methyl-2-hydroxy-5-[(4-methane sulfonyloxy-3-methoxycarbonylphenyl)azo]benzoate, prepared according to step (a), were hydrolized by boiling in 800 ml of 1N sodium hydroxide for 4 h. The hydrolized product was precipitated by addition of concentrated hydrochloric acid to pH of about 2. The precipitate was filtered and washed with water. Yield: 29.7 g (98%) of the title substance.

EXAMPLE 3

Disodium-3,3'-azo-bis(6-hydroxy-benzoate)

624 g of methyl-2-hydroxy-5-[(4-methane sulfonyloxy-3-methoxycarbonyl phenyl)-azo]benzoate, prepared according to step (a) of Example 2, were during 15 minutes added in portions to 3 liter of water and 428 g of sodium hydroxide while boiling. After boiling for 30 minutes 360 ml of acetic acid were added during 15 minutes to pH 6. The suspension was stirred for 1.5 h without cooling, the temperature falling to 70° C. After cooling to 30° C. the suspension was filtered and washed with 700 ml of methanol. After drying the title substance was obtained in a yield of 520 g (98.5%). The purity was >99.0% according to ion pair—liquid chromatographic analysis on a "reversed phase"-column ($\mu$-Bondapak $C_{18}$) using methanol/water (57:43) as eluant and tetrabutyl ammonium as counter ion.

What we claim is:

1. A method of preparing 3,3'-azo-bis-(6-hydroxy benzoic acid) of formula I

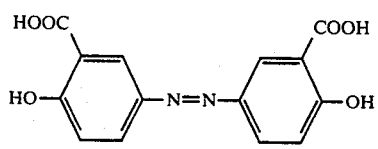

or salts thereof, comprising the steps of:
diazotizing a compound of formula II or a salt thereof

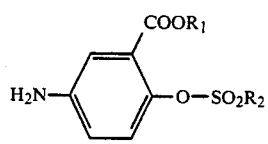

wherein $R_1$ is lower alkyl and $R_2$ is lower alkyl, phenyl or alkyl substituted phenyl, coupling the diazonium salt obtained in alkaline aqueous solution to a compound of formula III

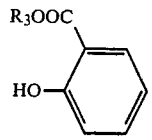

wherein $R_3$ is hydrogen or lower alkyl, to form a compound of formula IV

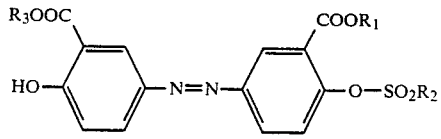

wherein $R_1$, $R_2$ and $R_3$ are as indicated above, and hydrolizing in alkaline medium the compound of formula IV, and isolating the compound of formula I or a salt thereof.

2. The method of claim 1, wherein the coupling of the diazonium salt of the compound of formula II to the compound of formula III is carried out in the presence of an alkali metal hydroxide.

3. The method of claim 1, further comprising the step of isolating and purifying the compound of formula IV before the alkaline hydrolysis.

4. The method of claim 3, wherein the purification of the compound IV is carried out by re-crystallization from an organic solvent.

5. The method of claim 1, wherein the hydrolysis of the compound of formula IV is carried out in the presence of an alkali metal hydroxide.

6. The method of claim 1, comprising the step of precipitating, after the hydrolysis of the compound of formula IV, the end compound of formula I or a salt thereof by lowing the pH of the reaction mixture.

7. The method of any one of claim 1, for preparing the di-sodium salt of the compound of formula I, comprising the steps of hydrolizing the compound of formula IV using sodium hydroxide and precipitating said disodium salt by neutralization to pH 5-8.

8. A method according to claim 1 wherein the compound of formula IV is purified by recrystallization before said hydrolyzing in an aqueous medium and the purity is at least 98%.

9. A method according to claim 8 wherein the purity of compound I is at least 98%.

10. A method according to claim 7 wherein the purity of compound I is at least 98%.

11. The method of claim 2 for preparing the disodium salt of the compound of formula I, comprising the steps of hydrolyzing the compounds of formula IV using sodium hydroxide and precipitating said disodium salt by neutralization to pH 5-8.

12. The method of claim 3 for preparing the disodium salt of the compound of formula I, comprising the steps of hydrolyzing the compounds of formula IV using sodium hydroxide and precipitating said disodium salt by neutralization to pH 5-8.

13. The method of claim 4 for preparing the disodium salt of the compound of formula I, comprising the steps of hydrolyzing the compound of formula IV using sodium hydroxide and precipitating said disodium salt by neutralization to pH 5-8.

14. The method of claim 5 for preparing the disodium salt of the compound of formula I, comprising the steps of hydrolyzing the compound of formula IV using sodium hydroxide and precipitating said disodium salt by neutralization to pH 5-8.

15. The method of claim 6 for preparing the disodium salt of the compound of formula I, comprising the steps of hydrolyzing the compound of formula IV using sodium hydroxide and precipitating said disodium salt by neutralization to pH 5-8.

16. 3,3'-azo-bis-(6-hydroxy benzoic acid) or salts thereof of at least 98% purity pharmaceutically acceptable purity.

* * * * *